US006176989B1

United States Patent
Shi

(10) Patent No.: US 6,176,989 B1
(45) Date of Patent: Jan. 23, 2001

(54) ELECTROCHEMICAL GAS SENSOR

(75) Inventor: Minglian Shi, Irvine, CA (US)

(73) Assignee: Teledyne Technologies Incorp., Los Angeles, CA (US)

( * ) Notice: Under 35 U.S.C. 154(b), the term of this patent shall be extended for 0 days.

(21) Appl. No.: 09/221,474

(22) Filed: Dec. 28, 1998

(51) Int. Cl.[7] .................................................. G01N 27/404
(52) U.S. Cl. .......................... 204/412; 204/415; 204/432; 205/783
(58) Field of Search ................................... 204/412, 415, 204/432, 431; 205/782.5, 783

(56) References Cited

U.S. PATENT DOCUMENTS

| 3,325,378 | * | 6/1967 | Greene et al. | 204/415 |
|---|---|---|---|---|
| 3,429,796 | | 2/1969 | Lauer . | |
| 3,438,872 | * | 4/1969 | Johansson | 204/405 |
| 3,503,861 | * | 3/1970 | Volpe | 204/412 |
| 3,929,587 | | 12/1975 | Gallagher . | |
| 4,152,233 | * | 5/1979 | Chand | 204/415 |
| 4,182,666 | | 1/1980 | Dickinson et al. . | |
| 4,288,544 | * | 9/1981 | Suzuki et al. | 204/415 |
| 4,326,927 | * | 4/1982 | Stetter et al. | 204/432 |
| 4,435,268 | * | 3/1984 | Martin et al. | 204/415 |
| 4,960,497 | | 10/1990 | Gallagher . | |
| 5,085,760 | | 2/1992 | Razaq et al. . | |
| 5,256,273 | | 10/1993 | Gallagher et al. . | |
| 5,393,392 | | 2/1995 | Masi . | |
| 5,395,507 | * | 3/1995 | Aston et al. | 204/432 |
| 5,453,172 | | 9/1995 | Alberti et al. . | |
| 5,556,533 | | 9/1996 | Nozoe et al. . | |
| 5,944,969 | * | 8/1999 | Scheffler et al. | 204/432 |
| 6,024,853 | * | 2/2000 | Kiesele et al. | 204/415 |

OTHER PUBLICATIONS

Ives et al, "Reference Electrodes", 1961 Month unavailable, pp. 333 and 334.*

* cited by examiner

Primary Examiner—T. Tung
(74) Attorney, Agent, or Firm—P. J. Viccaro

(57) ABSTRACT

An electrochemical gas sensor including a sensor body having a cavity, an electrolyte in the cavity, an auxiliary electrode in contact with the electrolyte, a sensing electrode in contact with the electrolyte, and a blocking electrode in contact with the electrolyte. At least a portion of the blocking electrode is positioned intermediate the auxiliary electrode and the sensing electrode, and the blocking electrode reduces electroactive materials within the electrolyte. Also disclosed is a method for sensing a partial pressure of a target gas in a sample gas, the method including introducing the sample gas into a gas sensor, applying different potentials to the auxiliary electrode, sensing electrode and blocking electrode, reducing electroactive materials present in the electrolyte to prevent the electroactive materials from contacting the sensing electrode, and outputting an electrical signal from the gas sensor representative of the target gas partial pressure.

20 Claims, 2 Drawing Sheets

ELECTROCHEMICAL GAS SENSOR

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to electrochemical gas sensors and, more specifically, to electrochemical gas sensors capable of sensing low partial pressure of a target gas. The present invention also relates to methods for sensing gas partial pressure, particularly at a low level of target gas.

2. Description of the Invention Background

Electrochemical gas sensors are used to sense a target gas content of a sample gas. Although the description of known electrochemical gas sensors in this application is directed towards the improvement of oxygen sensors in particular, the discussion is applicable to any type of electrochemical gas sensor.

A desirable electrochemical gas sensor should:

1. Provide zero output signal (zero offset) when target gas partial pressure (or concentration) is zero. This feature is more important when sensing a low level of a target gas, for example, in the 0–100 parts per billion range.
2. React rapidly to changes in target gas partial pressure.
3. Provide stable and repeatable output signals at all target gas partial pressures.

Typical electrochemical sensors include an anode and a cathode disposed in an electrolyte contained within a sensor body (cell). In a typical oxygen sensor, the output signal increases with the oxygen partial pressure in the sample gas. However, at near zero oxygen partial pressure levels, the output signal of the typical oxygen sensor often deviates significantly from the correct value due to a zero offset. The major contributing factors to this zero offset are impurities, including byproducts of the electrochemical reactions, that accumulate on the electrodes. Ionic impurities in the electrolyte or impurities that originate from the electrodes can lead to secondary electrochemical reactions at the electrodes. Upon deposition on the electrode, those impurities may also catalyze the reduction of hydrogen ions on the cathode. Those reactions are generally independent of the oxygen reduction process at the cathode generating sensor outputs even in the absence of oxygen.

Typical high sensitivity (ppm or ppb) electrochemical oxygen sensors are slow to recover their sensitivity after exposure to gases with a high oxygen partial pressure. During exposure to high oxygen partial pressure, the level of dissolved oxygen in the sensor electrolyte increases as a result of diffusion of oxygen from the sample gas into the electrolyte. Dissolved oxygen is reduced at the cathode in exactly the same manner as the oxygen from the sample gas thereby distorting the value of electrical current produced by the oxygen from the sample gas. The contribution to sensor current by dissolved oxygen generally decays with time. For typical electrochemical oxygen sensors, the time required for the sensor output to recover back to below a 1 ppm level after sensor exposure to atmospheric air could range from hours to days. To minimize the contributions of dissolved oxygen to the sensor output signal, oxygen free gases (zero gases) are often injected into and allowed to bubble through the electrolyte to reduce the level of dissolved oxygen in the electrolyte.

Since the output from an electrochemical oxygen sensor is dependent on the excitation potential at the cathode, a steady excitation potential is essential to achieving a stable and repeatable sensor output. For electrochemical oxygen sensors that are based on the fuel cell reactions, the excitation potential is derived from the redox reactions involving the anode material. There are many contributing factors to varying excitation potentials at the cathode of an oxygen sensor. For example, variations in temperature, redox reactant concentrations, and electrolyte electrical conductivity could affect the cathode potential. To overcome this issue, external power sources are often used to generate the necessary cathode potential. Circuitry such as a potentiostat circuit have been adopted by many skilled in the trade to provide the appropriate potentials to electrochemical sensors. The potentiostat approach necessitates the usage of high impedance op-amps and three electrodes for the sensor: the working electrode, the reference electrode, and the auxiliary (counter) electrode. For an oxygen sensor, oxygen is reduced at the working electrode. The reference electrode, carrying essentially no current, ensures that the excitation potential of the cathode remains constant. The potential of the auxiliary electrode will be automatically adjusted, through the potentiostat circuitry, to complete the redox reactions and maintain the working electrode potential. Although the potentiostat approach improves over a two electrode design by providing a more stable cathode excitation potential, it also does not address the zero offset and dissolved oxygen issues.

The foregoing problems associated with prior electrochemical gas sensors contribute to inaccurate readings as well as time varying sensor outputs. These problems are most pronounced when sensing low partial pressure of a target gas in the parts per billion (ppb) range. Accordingly, a need exists for an improved electrochemical gas sensor and for a target gas sensing method that permits accurate measurement of target gas partial pressure.

A galvanic or polarographic, electrochemical oxygen sensor includes an anode and a cathode disposed in an electrolyte within a sensor body. The electrical current flowing between the anode and cathode varies with the partial pressure of target gas present in the sample gas. The sensor detects oxygen as a result of electrochemical reduction of oxygen at the cathode (sensing electrode). For this to occur, an excitation electrical potential must be applied to the sensing electrode. This potential is generally selected so that all oxygen molecules reaching the sensing electrode are reduced immediately.

In a polarographic sensor, an anode and an external bias power supply are used to provide potential. A typical polarographic oxygen sensor employs a Ag/AgCl or $Ag/Ag_2O$ electrode (anode) along with an external bias potential of −0.7 to −0.8 V to drive the oxygen reduction at the sensing electrode. During the sensing process, oxygen is reduced at the sensing electrode while a proportional amount of silver is oxidized at the anode. AgCl and $Ag_2O$ are insoluble in the electrolyte and precipitate as an insulating thin film on the surface of the anode, limiting the Ag electrode from further participation in the electrochemical reactions. As a result, a large silver electrode is required in order to obtain a stable potential and a reasonable life span. The zero offset of such a polarographic sensor, due to the presence of dissolved oxygen and trace amount of $Ag^+$ ions in the electrolyte, is generally too high for measurement of oxygen partial pressure in the parts per million range.

A known galvanic oxygen sensor includes a lead electrode with zero external potential used to drive the oxygen reduction at the sensing electrode. The lead anode alone provides a suitable potential for oxygen reduction. However, sensors constructed this way suffer from long term output drift and excessive noise at the parts per billion oxygen level as a result of gradual accumulation of lead ions in the electrolyte. Cadmium, having a much lower solubility in the electrolyte, is often used to replace lead as an electrode material. Unfortunately, the excitation potential provided by the cadmium is not ideal for the oxygen reduction at the sensing electrode.

An oxygen sensor using two gas diffusion electrodes is also know in the art. A bias potential applied to these electrodes causes oxygen reduction at the sensing electrode and oxidation of water from the electrolyte at the anode. The advantage of this approach is that no by-product is generated during the oxygen sensing process. As a result, the composition of the electrolyte remains unchanged. The drawback of this approach is that the oxidation of water at the anode is sensitive to environmental conditions. Consequently, the anode in this arrangement is unable to provide a stable potential for the reduction of oxygen at the sensing electrode. This in turn limits this approach's oxygen reading consistency and accuracy at ppb levels.

Another known sensor replaces the water/oxygen anode with a hydrogen anode to prevent oxidation of water at the anode. However, the need to use hydrogen during operation is a nuisance and can be a safety hazard.

A sensor having an $Ni(OH)_2$/NiOOH anode is also known and used because such anode materials have low solubility in electrolyte. The low solubility of the $Ni(OH)_2$ and NiOOH, however, causes current through the anode to be blocked in a way similar to the blockage problems encountered with the Ag/AgCl, $Ag/Ag_2O$, and cadmium electrodes discussed earlier.

A known trace oxygen sensor that uses zero gas to purge the electrolyte in order to remove the dissolved oxygen creates a significant noise problem in the sensor output and often requires an expensive oxygen scrubber to produce the zero gas.

A method of removing dissolved oxygen in sensor electrolyte by introducing an additional pair of electrodes and an electrolyte reservoir exists. One of the electrodes (an anode) is located in the electrolyte reservoir, whereas the other electrode (a cathode) is located in the sensing chamber. By applying 1.5V dc potential across the two additional electrodes, active hydrogen generated on the cathode in the sensing chamber reacts with dissolved oxygen to form water. This technique requires a complicated sensor structure, and in some cases, gives rise to a negative sensor output signal due to the reaction of active hydrogen on the sensing electrode.

SUMMARY OF THE INVENTION

The present invention is directed to an electrochemical gas sensor. The sensor includes a body having a cavity containing an electrolyte. The sensor also includes a sensing electrode, an auxiliary electrode, a blocking electrode, and may include a reference electrode, all in contact with the electrolyte. The blocking electrode, positioned intermediate the sensing electrode and the auxiliary electrode may work independent of the sensing electrode to reduce electroactive materials and dissolved target gas in the electrolyte.

Another embodiment of the present invention is directed to an electrochemical gas sensor that includes a body having a cavity containing an electrolyte. The sensor also includes an auxiliary electrode, a sensing electrode and at least one reference electrode, each in contact with the electrolyte. Additionally, an output circuit is connected to the auxiliary electrode, the sensing electrode and the reference electrode. The output circuit has an amplifier circuit having an input and the reference electrode is connected directly to the input of the amplifier circuit.

The present invention is also directed to a method of sensing a partial pressure of a target gas in a sample gas. The method includes introducing the sample gas to a gas sensor. The gas sensor includes a sensing electrode and an auxiliary electrode, and may also include a blocking electrode or a reference electrode, all in contact with an electrolyte. The method also includes applying an electrical potential to the auxiliary electrode, reducing electroactive materials present in the electrolyte to prevent the electroactive materials from contacting the sensing electrode, and outputting an electrical signal from the gas sensor representative of the target gas partial pressure. The method may also include applying a potential to the blocking electrode to minimize the output of the sensor when it is exposed to a sample gas with zero target gas partial pressure.

The present invention is also directed to a method of sensing a partial pressure of a target gas in a sample gas that includes introducing the sample gas to a gas sensor. The gas sensor includes a sensing electrode, an auxiliary electrode, a reference electrode, and may include a blocking electrode all in contact with an electrolyte. The sensor also includes an output circuit that may be connected to the sensing electrode, the auxiliary electrode, and the reference electrode to ensure that sensing electrode potential remains constant regardless of target gas partial pressure as well as providing a signal that is representative of the partial pressure of the target gas. The method also includes applying an electrical potential to the auxiliary electrode, controlling the potential at the sensing electrode, minimizing electrical current flow through the reference electrode, and outputting an electrical signal from the gas sensor representative of the target gas partial pressure.

The present invention may be advantageously used in many applications, including sensing a low partial pressure of oxygen in the 0–100 parts per billion range. The present invention offers the advantage of being simple to manufacture, requiring little regular maintenance in operation, and having an extended useful life. The present invention also offers improved performance characteristics, including smaller signal offset, higher signal accuracy, reduced electrical noise, and faster signal response to target gas partial pressure variations. These and other advantages and benefits of the present invention will become apparent from the description hereinbelow.

BRIEF DESCRIPTION OF THE DRAWINGS

To aid in the understanding and practice of the present invention, it will be described in conjunction with the following figures, wherein.

DETAILED DESCRIPTION OF THE INVENTION

It is to be understood that the figures and descriptions of the present invention included herein illustrate and describe elements that are of particular relevance to the present invention, while eliminating, for purposes of clarity, other elements found in a typical electrochemical gas sensor of a known construction. Because the construction and implementation of such other elements are well known in the art, and because a discussion of them would not facilitate a better understanding of the present invention, such a discussion is not provided herein. It is also to be understood that the embodiments of the present invention that are described herein are illustrative only and are not exhaustive of the manners of embodying the present invention. For example, it will be recognized by those skilled in the art that the present invention may be readily adapted to function in conjunction with amperometric sensors, with sensors that operate on oxidation and reduction principles, and with sensors that detect partial pressure or concentrations of target gases other than oxygen.

Figure 1:
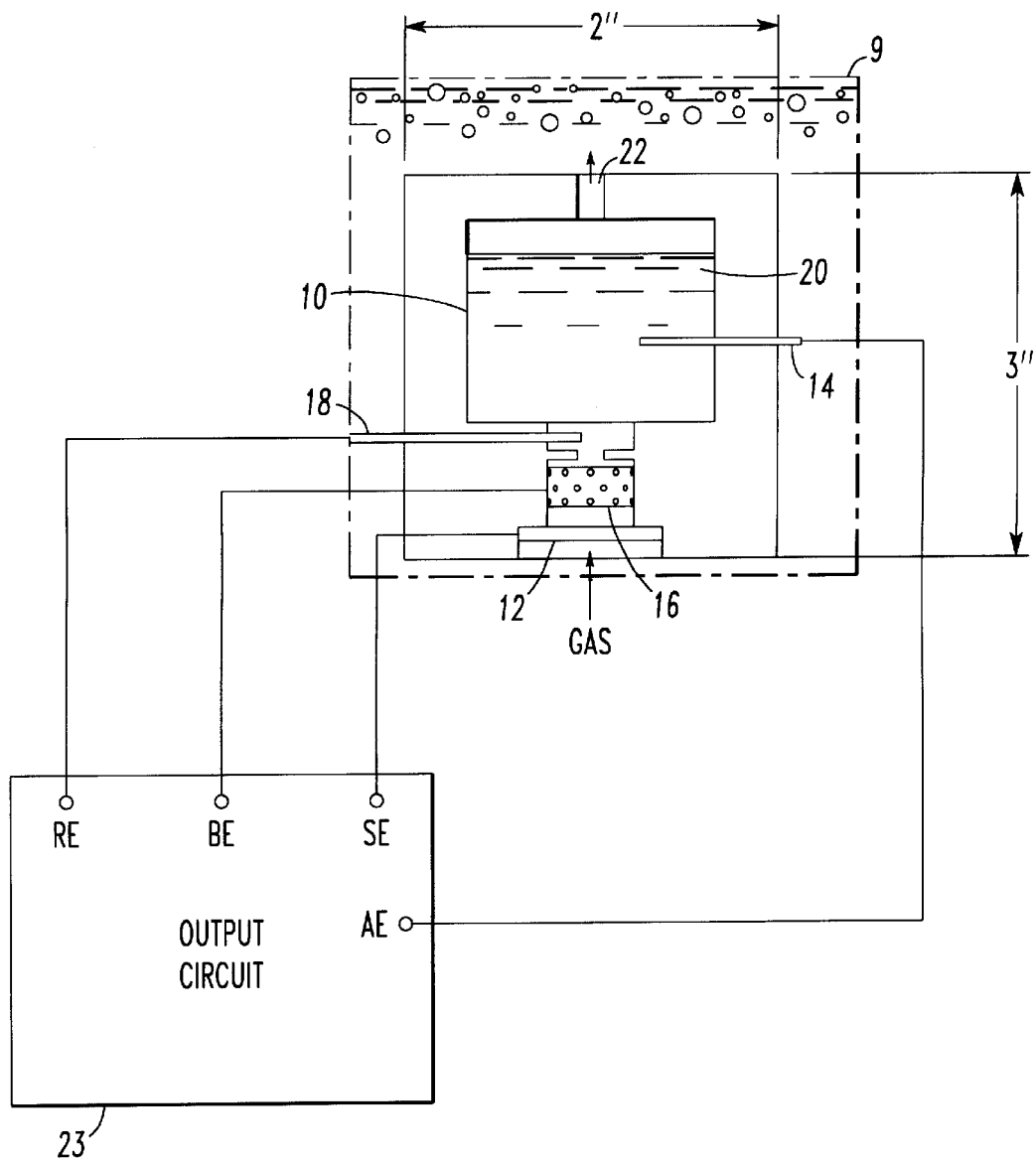
FIG. 1 is a representation in cross-section of an embodiment of the electrochemical gas sensor of the present invention.

FIG. 1 is a cross-sectional view of an electrochemical oxygen gas sensor 9 constructed according to the present invention and including a body 10, a sensing electrode 12, an auxiliary electrode 14, a blocking electrode 16, a reference electrode 18, and an electrolyte 20. The electrolyte may be an ionic conductor appropriate for the sensor operation. A sample gas, which may include oxygen (the target gas), is brought in contact with the sensing electrode 12. Oxygen that contacts the sensing electrode 12 enters and exits the sensor 9 as indicated by the arrows. The components of the sensor 9 may be constructed of a variety of materials and in many dimensions. The materials and dimensions of the sensor 9 are illustrative only and are not exhaustive of the manners of embodying the present invention. The body 10 includes an interior cavity for containing the electrolyte 20, and the electrodes 12, 14, 16, and 18 of the present invention are placed in communication with the electrolyte 20. A portion of each electrode 12, 14, 16, and 18 may extend through the sensor body 10 for connection to external circuitry. The body 10 may include a vent, such as vent 22, through which "spent" target gas and gaseous impurities may be released. The vent 22 may include a selectively porous material, for example, Teflon, to allow the target gas to exit the sensor 9 while limiting the transfer of contaminants into the electrolyte 20. The body 10 itself may be formed from an electrically insulating material such as, for example, plastic.

The electrolyte 20 may be any substance that provides the appropriate ionic conductivity consistent with the reduction/oxidation processes chosen for the sensing of the target gas at the sensing electrode 12. For example, potassium hydroxide based electrolytes are suitable when oxygen is the target gas. Suitable electrolytes for sensing a particular target gas will be readily apparent to those of ordinary skill in the art.

The sensing electrode 12 is disposed within the body 10 such that it is in contact with both the electrolyte 20 and the sample gas. In addition to effecting the electrochemical reactions, the sensing electrode 12 must also facilitate the delivery of the target gas and preferably minimize the evaporation of the electrolyte 20 to the sample gas. Candidates for the sensing electrode 12 include, for example, the gas diffusion electrode of sensor 9 or a noble metal electrode covered with a gas permeable, hydrophobic membrane. The sensing electrode 12 should be constructed of materials that are relatively chemically inert, for example, carbon, silver, gold, and platinum. As used herein, the term "chemically inert" refers to materials that do not readily react with other materials, whether in gaseous, liquid, or solid form, that will be encountered during the operation of the sensor 9 and under conditions in which the sensor 9 is to be used.

When the sensing electrode 12 is appropriately biased with respect to the electrolyte 20, the target gas will be reduced (or oxidized depending on the design of the electrochemical sensor). In the case of an oxygen sensor, oxygen from the gas sample is reduced at the sensing electrode 12 when the sensing electrode 12 is biased at a potential of −0.7 to −1.0 volt. The reduction of each oxygen molecule at the sensing electrode 12 draws 4 electrons from the external circuitry. As a result, the current i associated with the reduction of oxygen as sensed by the external circuitry can be expressed as:

$$i=4Fv$$

where F is the Faraday constant and v is the molar amount of oxygen molecules reaching the sensing electrode 12 per second. The rate of oxygen molecules reaching the sensing electrode 12, limited by diffusion through a diffusion barrier of the gas diffusion electrode, can be expressed as:

$$v=D\delta^{-1}AP_{O2}$$

where D is the diffusion coefficient of oxygen gas through a diffusion barrier, δ is the thickness of the diffusion barrier, A is the surface area of the diffusion barrier, and $P_{O2}$ is the oxygen partial pressure in the sample gas. Where the sample gas pressure is constant, $P_{O2}$ can indicate the oxygen concentration in the sample gas. Utilizing these two equations, one can arrive at an expression for the oxygen reduction current i, as shown in the following equation:

$$i=4FD\delta^{-1}AP_{O2}$$

that is directly proportional to the pressure of oxygen in the sample gas.

When sensing a trace level of a target gas, the construction of the sensing electrode 12 may include a gas diffusion electrode, which has a high gas diffusion coefficient which is a result of its porosity. A higher diffusion coefficient provides a larger sensor current and hence a more favorable signal to noise ratio.

As oxygen molecules are reduced at the sensing electrode 12 in the presence of water, hydroxyl ions ($OH^-$) are formed. When an adequate potential is applied at the auxiliary electrode 14, the hydroxyl ions are oxidized to form oxygen. To ensure that there is no accumulation of hydroxyl ions at the sensing electrode 12 or depletion of hydroxyl ions at the auxiliary electrode 14, the sensor 9 must allow the hydroxyl ions to move freely through the electrolyte 20.

The auxiliary electrode 14 may be constructed out of chemically inert material, such as, for example, carbon or noble metals, so that it generates no byproducts other than oxygen. The oxygen generated at the auxiliary electrode 14 is typically dissolved in the electrolyte, enriching the concentration of dissolved oxygen surrounding the auxiliary electrode 14. Eventually, the oxygen migrates to the surface of the electrolyte 20 and is released to the atmosphere above the electrolyte 20 through the vent 22 in the body 10.

Oxygen generated at the auxiliary electrode 14 and oxygen from the atmosphere above the electrolyte 20 tend to diffuse through the electrolyte 20 toward the sensing electrode 12. To ensure that only the oxygen from the sample gas is reduced at the sensing electrode, a blocking electrode 16 is immersed in the electrolyte 20 and located between the sensing electrode 12 and auxiliary electrode 14. By biasing the blocking electrode 16 at a potential the same as or slightly more negative than the sensing electrode 12, the blocking electrode 16 intercepts and reduces the dissolved oxygen from the auxiliary electrode 14 and the atmosphere above the electrolyte 20.

For the sensor 9 to function properly, the blocking electrode 16 must allow "inert" ions such as $K^+$ and $OH^-$ to diffuse through it freely. To this end, the blocking electrode 16 may be constructed of chemically inert, porous electrical conductors such as porous carbon or multi-layers of noble metal mesh. Its porosity and thickness affect the overall effectiveness of the blocking electrode 16. Use of multiple electrodes may also enhance the effectiveness of the blocking electrode 16. Optimization of the geometry and the choice of number of the blocking electrodes 16 are best accomplished through experimentation. A single block of commercially available porous carbon 0.5 cm to 1.0 cm thick has been found to perform satisfactorily.

It is advantageous to locate the blocking electrode 16 as close to the sensing electrode 12 as possible in order to minimize the volume of electrolyte 20 that could act as a reservoir for dissolved oxygen whenever the sensor 9 is exposed to a high level of oxygen. After prolonged exposure to a high level of oxygen, the level of dissolved oxygen in the electrolyte 20 in the immediate vicinity of the sensing electrode 12 can be high. The sensor output generated by the dissolved oxygen can mask the output signal produced by a subsequent low level of oxygen in the sample gas. This masking process continues until the dissolved oxygen is consumed. Reducing the volume of electrolyte 20 between the sensing electrode 12 and the blocking electrode 16 therefore improves the recovery time of the sensor 9 after exposure to a high level of oxygen.

In addition to minimizing the amount of dissolved oxygen reaching the sensing electrode 12, the blocking electrode 16 inhibits the sensing electrode 12 from sensing electroactive materials in the electrolyte 20. As used herein, an "electroactive" material refers to an ion or molecule that may be reduced or oxidized at the potential of the sensing electrode. The electroactive materials could be impurities in the electrolyte 20 when it is first introduced into the sensor body 10, or can be derived from electrochemical reactions at the various electrodes. An example of an electroactive material would be the trace level of $Ag+$ ions from the reference electrode 18. The blocking electrode 16 therefore ensures that the sensing electrode 12 will only sense oxygen from the sample gas.

The reference electrode 18 allows accurate control of the sensing electrode 12 potential by minimizing its polarization. Constructed of a reversible electrochemical couple, for example, silver/silver oxide, the reference electrode 18 is disposed in the electrolyte 20 at a point near the sensing electrode 12. Through the use of high impedance op-amps, the reference electrode 18 carries essentially no current. As a result, the reference electrode 18 attains effectively the potential of the electrolyte 20 and helps to define the optimum voltage required for the sensing of the sample gas at the sensing electrode 12. For the embodiment of FIG. 1, the reference electrode 18 may be, for example, a piece of silver wire coated with silver oxide if the electrolyte 20 is made up of potassium hydroxide or it may be a silver wire coated with silver chloride if the electrolyte 20 contains chloride ions. Other variations of geometry, electrode materials, and electrolytes will be readily apparent to those of ordinary skill in the art on considering the present detailed description of the invention.

The sensor body, which may be constructed of electrically insulating material, such as, for example, plastics, defines the physical relationships of the various sensor components including the electrodes 12, 14, 16, and 18. For trace level measurements of a target gas, for example, trace oxygen, it is imperative that the leak rate of the target gas into the interior of the sensor 9 through the sensing electrode 12 is low. This ensures that the signal generated by the target gas leaked previously into the interior of the sensor body 10 is insignificant compared to the signal generated directly by the target gas from the sample gas.

The electrodes 12, 14, 16, and 18 of the present invention are connected to an output circuit 23, at terminals SE, AE, BE, and RE respectively. The output circuit 23 permits interaction between the electrodes 12, 14, 16, and 18, and provides electrical output signals, corresponding to attributes sensed by the sensor 9, that may be read by external means.

Figure 2:
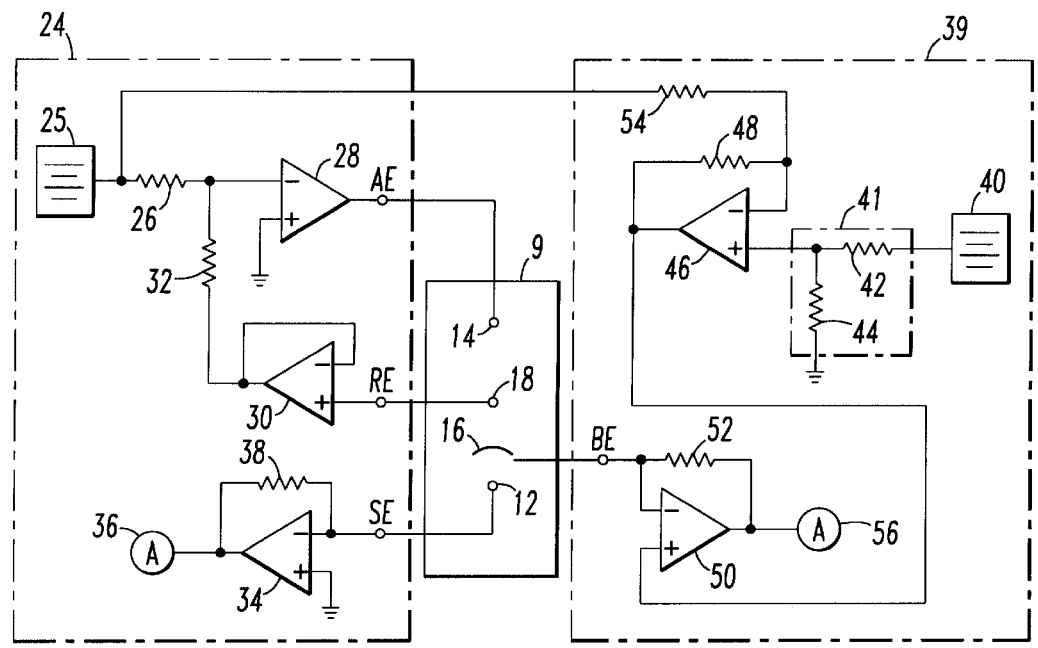
FIG. 2 is a diagram illustrating an output circuit for the electrochemical gas sensor of FIG. 1.

FIG. 2 is a diagram illustrating an output and control circuit 23 for use with the sensor 9 illustrated in FIG. 1. The output and control circuit 23 is made up of a target gas output circuit 24 and a blocking electrode bias control circuit 39. The operation of these circuits is straightforward and will be readily apparent to those skilled in the art of basic electronics. As a result, only a general description of circuit 23 is provided herein.

The output circuit 24 provides control of the potential of the sensing electrode 12 through the reference electrode 18, thereby ensuring that the sensor output is accurate at various target gas levels. It also provides an output signal, corresponding to the target gas partial pressure, which originates at the sensing electrode 12. The target gas output circuit 24 also minimizes current flow through the reference electrode 18 so as to minimize the voltage drop at the interface between the reference electrode 12 and electrolyte 20.

The target gas output circuit power supply 25 is connected to the negative input of operational amplifier 28 via resistor 26. The output of operational amplifier 30 is also connected to the negative input of operational amplifier 28 via resistors 32. By connecting the negative input directly to the output of operational amplifier 30, the positive input terminal to operational amplifier 30 has effectively the same potential as its output potential. The reference electrode 18 is connected to the positive input terminal of operational amplifier 30. Resistors 26 and 32 have the same resistance. There is an equivalent resistor inside the sensor between the reference electrode and the auxiliary electrode, completing a feedback loop for operational amplifier 28. The positive input of operational amplifier 28 is at the true ground, and the negative import is at a virtual ground. This arrangement enables the reference electrode to assume the same potential as the output voltage of the target gas output circuit power supply 25, but with a polarity opposite that of the power supply 25. The high input resistance associated with operational amplifier 30 also ensures that minimal current flows between the reference electrode 18 and electrolyte 20.

The current collected by the auxiliary electrode 14 is the sum of the current through the sensing electrode 12 and the current through the blocking electrode 16. The feedback circuitry formed by amplifiers 28 and 30 and resistors 26 and 32 provide adequate voltage for the auxiliary electrode 14 to accommodate the current from the sensing electrode 12 and the current from the blocking electrode 16. As the current through the sensing electrode 12 and the current through the blocking electrode 16 vary during normal operation of the sensor, the output voltage of operational amplifier 28 also changes automatically to meet the requirement of carrying current.

The blocking electrode bias control circuit 39 provides control of the potential of the blocking electrode 16 and a signal that corresponds to the current collected by the blocking electrode 16. This signal can be used to monitor the quality of the electrolyte 20. The blocking electrode bias control power supply 40 is attached to the positive input of operational amplifier 46 via resistor 42 to control the potential of the blocking electrode 16. Resistor 54 may have the same resistance as resistor 48, resistor 42 may have the same resistance as resistor 44, and the power supply 40 may have the same output voltage as the target gas output circuit power supply 25, in which case the potential of the blocking electrode 16 will be the same as the potential of the sensing electrode 12.

For optimal operation of the blocking electrode 16 in an electrochemical oxygen sensor, its potential should be set at a level that is the same as, or slightly more negative than, the potential at the sensing electrode 12. A satisfactory potential range for the blocking electrode 16 has been found to be 0 to 500 millivolts less than the potential of the sensing electrode 12. This implies that the blocking electrode bias control power supply 40 is typically set at a slightly lower output value than the target gas output circuit power supply 25. The optimal blocking electrode potential may be determined when the sensor output is at a minimum in the presence of a zero gas, i.e., a sample gas with zero concentration of the target gas.

Figure 3:
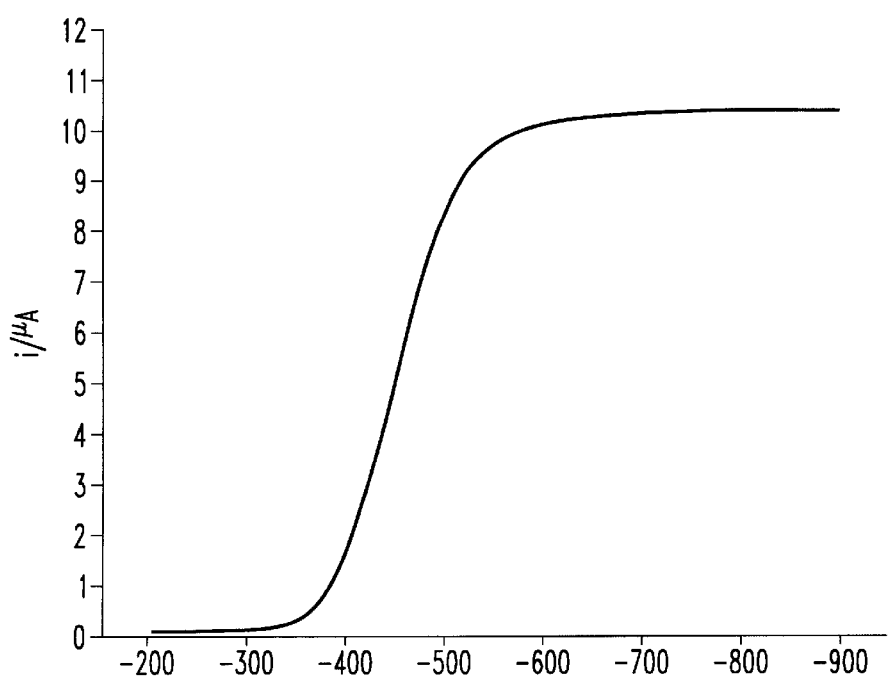
FIG. 3 is a polarization curve for oxygen in a 10% potassium hydroxide electrolyte in an oxygen sensor constructed according to the present invention, relating the sensor output to the potential of the sensing electrode.

In one embodiment of the present invention for the measurement of a low level of oxygen, Model LT1014 operational amplifiers manufactured by Linear Technology are utilized as operational amplifiers 28, 30, 46, and 50. A Model MAX430 operational amplifier, manufactured by Maxim, is utilized as operational amplifier 34. Resistors 26, 32, 42, 44, 48, and 54 are 10 k ohm resistors. The resistance of resistor 38 depends on the oxygen range to be sensed and the sensitivity of the sensing electrode 12. In this embodiment, a 1M ohm resistor may be used when sensing oxygen in the 0–100 parts per billion range. Using a 10% potassium hydroxide (on a weight/volume basis in units of grams/milliliter) electrolyte, the target gas output circuit power supply 25 is typically set at an output of –0.7 to –1.0 volt. Setting of the output of the target gas output circuit power supply 25 is based on the polarization curve of oxygen reduction at the sensing electrode 12. FIG. 3 illustrates the variation of the sensing electrode 12 current at different target gas output circuit power supply 25 voltages. At –0.7 to –1.0 volt, the sensing electrode 12 current is insensitive to power supply 25 voltage changes and varies only when the target gas partial pressure changes.

When offset correction for the sensing electrode 12 and the monitoring of the electrolyte quality are not required, the blocking electrode 16 can be connected directly to the ground of circuit 23. In that case, the blocking electrode 16 acts not only as a chemical shield but also acts as an electronic shield to the sensing electrode 12, resulting in an even lower noise level for the sensor output signal at terminal 36 in the target gas output circuit 24.

The present invention also includes a method for sensing a target gas in a sample gas. The method includes introducing a sample gas, having a target gas partial pressure into an electrochemical gas sensor 9. The method also includes applying a well-defined and constant voltage to the sensing electrode 12 to achieve accurate detection of the target gas and to apply the necessary potential to the auxiliary electrode. The method further includes using a blocking electrode 16 to minimize the effects of dissolved target gases and to prevent electroactive materials from contacting the sensing electrode 12. The method includes as an option outputting a signal that is representative of the level of impurities and dissolved target gas concentration in the electrolyte 20.

Those of ordinary skill in the art will recognize that many modifications and variations of the present invention may be implemented. The foregoing description and the following claims are intended to cover all such modifications and variations. Furthermore, the materials and processes disclosed are illustrative of the invention, but are not exhaustive. Other materials and processes may be employed to utilize the present invention and will be apparent to one of ordinary skill upon consideration of the present description of the invention.

What is claimed is:

1. An electrochemical oxygen sensor comprising:
   a body having a cavity;
   an electrolyte in said cavity;
   an auxiliary electrode in contact with said electrolyte;
   a sensing electrode in contact with said electrolyte;
   a porous carbon blocking electrode positioned intermediate said auxiliary electrode and said sensing electrode and having a thickness of at least 0.5 cm in a direction in which said auxiliary electrode is separated from said sensing electrode, said blocking electrode reducing electroactive materials within said electrolyte; and
   a reference electrode in contact with said electrolyte and positioned intermediate said auxiliary electrode and said sensing electrode, said reference electrode comprising a material including silver.

2. The electrochemical gas sensor of claim 1, wherein said auxiliary electrode, said sensing electrode, and said blocking electrode are mounted on said body.

3. The electrochemical gas sensor of claim 1, wherein said reference electrode is mounted on said body.

4. The electrochemical gas sensor of claim 1, wherein said reference electrode provides an electrical reference for said sensing electrode and said blocking electrode.

5. The electrochemical gas sensor of claim 1, further comprising an output circuit for generating an output through said blocking electrode.

6. The electrochemical gas sensor of claim 5, wherein said output generated through said blocking electrode corresponds to the concentration of electroactive materials present in the electrolyte.

7. The electrochemical gas sensor of claim 1, further comprising an output circuit for generating an output through said sensing electrode.

8. The electrochemical gas sensor of claim 7, wherein said electrochemical gas sensor senses the partial pressure of a target gas in a sample gas, and wherein said sensing electrode output varies with the target gas partial pressure of the sample gas.

9. The electrochemical gas sensor of claim 1, wherein said sensing electrode comprises a gas diffusion electrode.

10. The electrochemical gas sensor of claim 1, wherein said sensing electrode comprises a membrane covered noble metal electrode.

11. The electrochemical gas sensor of claim 1, wherein said auxiliary electrode comprises a material selected from the group consisting of a noble metal and carbon.

12. The electrochemical gas sensor of claim 1, wherein said electrochemical gas sensor senses the partial pressure of oxygen in the sample gas.

13. The electrochemical gas sensor of claim 1, wherein oxygen is created as a byproduct at said auxiliary electrode.

14. The electrochemical gas sensor of claim 1, wherein said electrolyte comprises potassium hydroxide, and wherein said reference electrode comprises silver and silver oxide.

15. The electrochemical gas sensor of claim 1, wherein said electrolyte comprises potassium chloride and wherein said reference electrode comprises silver and silver chloride.

16. The electrochemical gas sensor of claim 1, further comprising a circuit through which sensing electrode potential and blocking electrode potential may be independently adjusted.

17. The electrochemical gas sensor of claim 1, wherein the blocking electrode has an electrical potential and the sensing electrode has an electrical potential that is greater than the electrical potential of the blocking electrode.

18. An oxygen sensor comprising:
   a body having a cavity;
   an electrolyte in said cavity;
   a sensing electrode, in contact with said electrolyte, reducing oxygen at said sensing electrode to produce hydroxyl ions;
   an auxiliary electrode, in contact with said electrolyte, oxidizing hydroxyl ions;
   a porous carbon blocking electrode in contact with said electrolyte, at least a portion of said blocking electrode positioned intermediate said auxiliary electrode and said sensing electrode, wherein said blocking electrode has a thickness of at least 0.5 cm in a direction in which said auxiliary electrode is separated from said sensing electrode, said blocking electrode reducing electroactive materials within said electrolyte; and
   a reference electrode in contact with said electrolyte and positioned intermediate said auxiliary electrode and said sensing electrode, said reference electrode comprising a material including silver.

19. An electrochemical gas sensor for sensing a partial pressure of oxygen in a sample gas, the electrochemical gas sensor comprising:
   a sensor body having a cavity and a vent;
   an electrolyte disposed in said cavity of said sensor body;
   a sensing electrode, mounted on said sensor body and in contact with said electrolyte, said sensing electrode reducing oxygen to produce hydroxyl ions;
   an auxiliary electrode mounted on said sensor body and in contact with said electrolyte, said auxiliary electrode oxidizing hydroxyl ions;
   a porous carbon blocking electrode mounted on said sensor body, at least a portion of said blocking electrode positioned intermediate said sensing electrode and said auxiliary electrode and having a thickness of at least 0.5 cm in a direction in which said auxiliary electrode is separated from said sensing electrode, said blocking electrode reducing electroactive materials that contact said blocking electrode;
   a reference electrode mounted on said sensor body and positioned intermediate said auxiliary electrode and said sensing electrode, said reference electrode controlling a potential at said sensing electrode and providing an electrical reference for said blocking electrode and said reference electrode comprising a material including silver;
   a circuit generating an output through said sensing electrode; and
   a circuit generating an output through said blocking electrode.

20. An electrochemical gas sensor for sensing a partial pressure of oxygen in a sample gas, the electrochemical gas sensor comprising:
   means for introducing the sample gas to the electrochemical gas sensor;
   an auxiliary electrode mounted on the electrochemical gas sensor;
   means for applying electrical potential to said auxiliary electrode;
   a sensing electrode mounted on the electrochemical gas sensor;
   an electrolyte contained within the electrochemical gas sensor;
   a porous carbon blocking electrode positioned intermediate said auxiliary electrode and said sensing electrode and having a thickness of at least 0.5 cm in a direction in which said auxiliary electrode is separated from said sensing electrode, for reducing electroactive materials present in said electrolyte;
   a reference electrode in contact with said electrolyte and positioned intermediate said auxiliary electrode and said sensing electrode, said reference electrode comprising a material including silver; and
   means for outputting an electrical signal from the gas sensor representative of the target gas partial pressure.

* * * * *

UNITED STATES PATENT AND TRADEMARK OFFICE
CERTIFICATE OF CORRECTION

PATENT NO. : 6,176,989 B1
DATED : January 23, 2001
INVENTOR(S) : Minglian Shi

It is certified that error appears in the above-identified patent and that said Letters Patent is hereby corrected as shown below:

<u>Column 3,</u>
Line 15, delete "know" and substitute therefore -- known --.

Signed and Sealed this

Fifteenth Day of June, 2004

JON W. DUDAS
*Acting Director of the United States Patent and Trademark Office*